United States Patent [19]

Cremona-Bonato

[11] Patent Number: 4,644,946
[45] Date of Patent: Feb. 24, 1987

[54] STUMP SHRINKING APPARATUS FOR ABOVE KNEE AMPUTEES

[76] Inventor: G. Cremona-Bonato, 2930 Scott Rd., Burbank, Calif. 91504

[21] Appl. No.: 776,120

[22] Filed: Sep. 13, 1985

[51] Int. Cl.⁴ .............................................. A61F 13/00
[52] U.S. Cl. .................................................. 128/165
[58] Field of Search ................. 128/165, 157, 171, 78, 128/80 R, 89 R, 506, 518 B, 518 R, 519, 524, DIG. 15, DIG. 20

[56] References Cited

U.S. PATENT DOCUMENTS

| | | | |
|---|---|---|---|
| 2,312,632 | 3/1943 | Drew | 297/6 |
| 3,032,035 | 5/1962 | Dempsey | 128/165 |
| 3,138,156 | 6/1964 | Crowell et al. | 128/157 |
| 3,490,449 | 1/1970 | Ewerwahn | 128/157 |
| 3,490,450 | 1/1970 | Gardner | 128/171 X |
| 3,515,136 | 6/1970 | Baker | 128/171 X |
| 3,741,202 | 6/1973 | Morgan | 128/171 |
| 3,779,550 | 12/1973 | Benoun | 128/89 R |
| 4,057,056 | 11/1977 | Payton | 128/89 R |

*Primary Examiner*—Gregory E. McNeill
*Attorney, Agent, or Firm*—James E. Brunton

[57] ABSTRACT

A post surgical appliance for applying shrinking pressure to the stump of an above the knee amputee. The appliance comprises an elongated, side opening elastic support panel which encircles the lower abdominal, or lumbar region, and the upper thigh portion of the amputee. Uniform compressive pressure is applied to the stump by uniquely configured, crossing elastic straps which are secured to the support panel. These straps exert a uniform, upwardly directed constant pressure on the end and lower sides of the stump. For ease of use, one end of each of the straps is secured to the front of the panel with the opposite ends being releasably secured to the posterior of the panel by self securing fastening materials.

7 Claims, 5 Drawing Figures

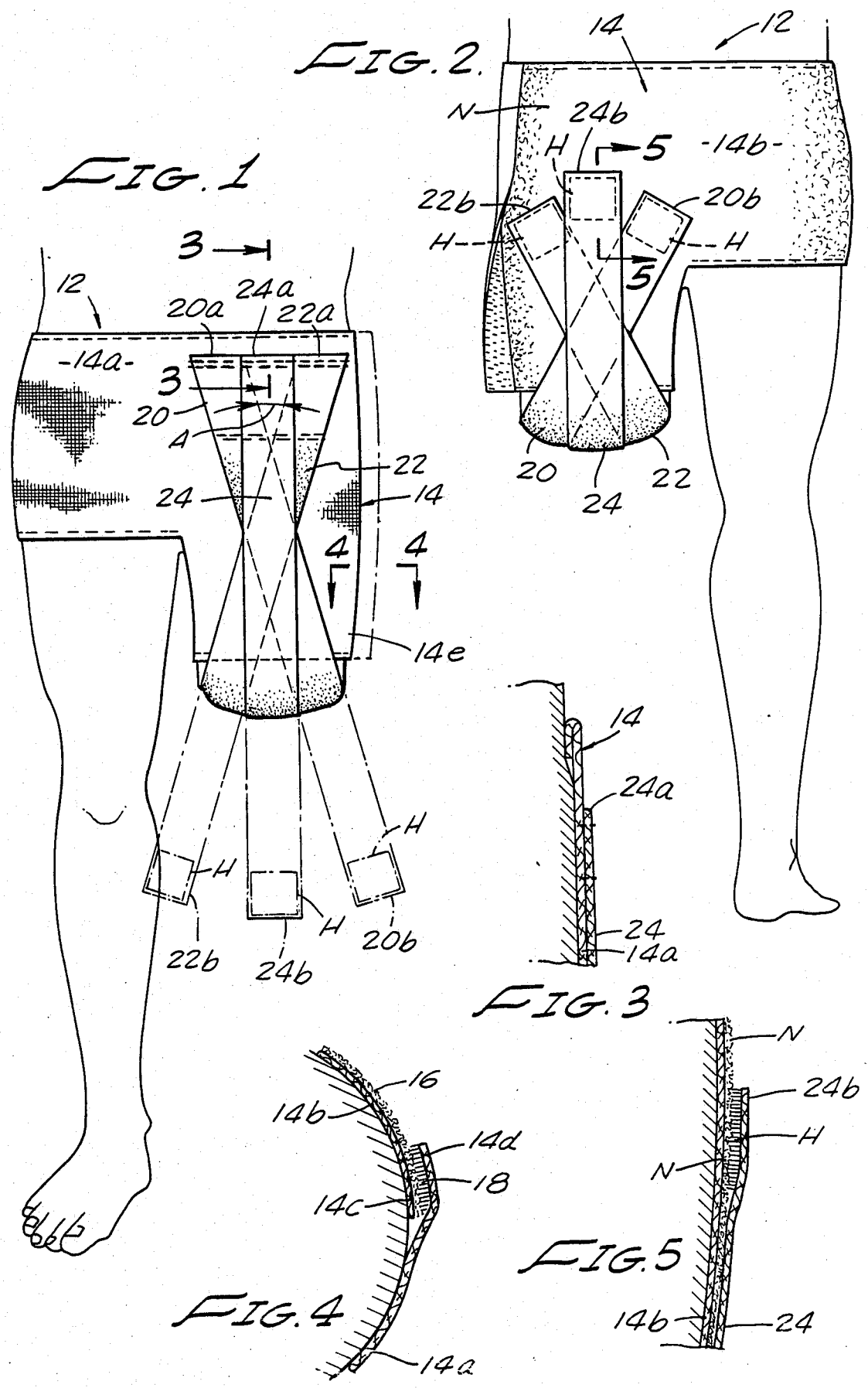

STUMP SHRINKING APPARATUS FOR ABOVE KNEE AMPUTEES

BACKGROUND OF THE INVENTION

1. Field of the Invention

The present invention relates generally to post-surgical appliances. More particularly, the invention concerns an improved, immediate post-surgical pressure applying apparatus for applying a shrinking pressure to the stump of an above the knee amputee.

2. Discussion of the Prior Art

Following a leg amputation it is desirable to shrink or reduce the cross sectional size of the stump to facilitate fitting of a prosthetic appliance. In the past, various approaches have been suggested to perform this function.

In past years a common expedient to accomplish shrinking of the stump was the application of surgical bandages. However, this type of bandaging, if it is to be effective, must be done by trained personnel and is time consuming, both in applying and removing the bandages.

More recent approaches for stump shrinking include the use of devices of the character having waist and shoulder straps adapted to carry means for adjustably connecting wrapping bandages thereto. Exemplary of such a device is that disclosed in U.S. Pat. No. 3,032,035 to Dempsey. This device comprises a body encircling belt, a shoulder belt connected to the belt and wrapping bandages connected to the belt by means of bandage retaining cleats and front and rear suspension straps. However, apparatus embodying multiple straps, harnesses, buckles and the like are usually difficult to use and generally require assistance both in application and removal.

Another type of stump shrinking apparatus is disclosed in U.S. Pat. No. 3,130,156 to Crowell. This apparatus comprises a sleeve member means forming a pocket adjacent the lower portion of the sleeve and a plurality of straps secured to the sleeve and adapted to pull the sleeve upwardly to force a pad carried within the sleeve against the stump.

Other prior art devices for use in shrinking the stump of leg amputees include devices which make use of elastic stockings, or tube like members, which are tied at the bottom, or are closed by use of surgical bandages. The disadvantage of these latter types of devices is that the stump portion is totally encapsulated preventing air circulation and making post surgical treatment of the stump area difficult.

As will be appreciated from the discussion which follows, the present invention effectively overcomes the drawbacks of the prior art devices by providing a uniquely designed, simple to use device specially adapted for use by above knee amputees.

SUMMARY OF THE INVENTION

It is an object of the present invention to provide a post surgical appliance for applying uniform, compressive, shrinking forces to the stump of an above knee amputee which is easy to apply and remove from the amputee without assistance from trained personnel.

Another object of the invention is to provide an appliance the aforementioned character in which the degree of the compressive forces being exerted on the stump can be quickly and easily adjusted and in which the end of the stump can be quickly exposed for treatment.

Another object of the invention is to provide such an appliance which is of unitary design and includes self securing fastening means which enables the appliance to be applied and removed by either the amputee or by unskilled hospital attendants.

Still another object of the invention is to provide an appliance of the class described in the preceding paragraphs which is comfortable to wear and yet will remain in position on the patent without the need for frequent adjustment.

A further object of the invention is to provide an appliance of the aforementioned character in which compressive pressure is applied to the stump by uniquely configured, crossing elastic straps which are secured to a side opening, elongated panel adapted to encircle the lower abdomen and upper thigh portion of the patient. The elastic straps adjustably exert a uniform, upwardly directed constant pressure on the end and lower sides of the stump leaving the upper side portions thereof exposed. For ease of use, one end of each of the straps is secured to the front of the panel with the opposite ends being releasably secured to the posterior of the panel.

Still another object of the invention is to provide a device as described in the preceding paragraphs which is compact, durable, and inexpensive to manufacture.

BRIEF DESCRIPTION OF THE DRAWINGS

FIG. 1 is a front view of the device of the invention shown as it would appear in position on an above knee amputee.

FIG. 2 is a rear view of the device shown as it would appear in position on an above knee amputee.

FIG. 3 is an enlarged cross-sectional view taking along lines 3—3 of FIG. 1.

FIG. 4 is an enlarged cross-sectional view taken along lines 4—4 of FIG. 1.

FIG. 5 is a greatly enlarged cross-sectional view taking along lines 5—5 of FIG. 2.

DESCRIPTION OF THE INVENTION

Referring to the drawings, and particularly to FIGS. 1 and 2, the appliance of the present invention for applying compressive forces to the stump of an above the knee amputee is generally designated by the numeral 12. In this form of the invention, the device comprises an elongated support panel 14 of a stretch material for encircling the lower abdominal portion, or lumbar region, of the amputee. Support panel 14 has front and rear surfaces, 14a and 14b, and overlapping end, or edge, portions 14c and 14d (FIG. 4). First fastening means are carried by one of the overlapping edge portions 14c or 14d and second fastening means are carried by the other of the overlapping edge portions. These fastening means cooperate to releasably interconnect the edge portions of the support panel together so as to securely affix it in position about the lumbar region of the amputee in the manner shown in FIGS. 1 and 2.

Referring to FIG. 4, the first and second fastening means here comprise self-gripping fastening means of the Velcro type. As indicated in FIG. 4, in this embodiment of the invention, a nap-surface 16 is provided on edge portion 14c while a hook portion 18 is provided on edge portion 14d.

The Velcro type, self-securing fastening means is well known in the art and is readily available commercially. The Velcro product is provided in the form of complementary fabric sections, one of which mounts a plurality of closely spaced rows of small plastic hooks (herein referred to as the hook surface) and the other carries a surface having an upstanding nap (herein referred to as the nap surface). When these Velcro sections are pressed together in a face-to-face relationship, the tiny hooks grip the nap surface and firmly secure the fabric sections together until they are released by manually pulling the sections apart in a direction normal to their engaged surfaces.

Turning once again to FIGS. 1 and 2, in the present form of the invention, the apparatus also includes an upper thigh encircling portion 14e which is made of a stretch material and depends from one side of the elongated support panel 14. This thigh encircling portion 14e can, of course, be provided on either side of the support panel 14 depending upon which leg of the amputee has been amputated. Preferably, the thigh encircling portion is made of the same material as the support panel and is constructed integrally therewith.

As best seen in FIG. 1, the upper thigh encircling portion of the device strategically ends at a location above the beginning of the stump portion of the amputee. With this construction the upper thigh encircling portion 14e, in cooperation with the front and rear surfaces 14a and 14b of the elongated panel cooperate to hold the device securely in position on the patient without covering or interfering with the stump. Because the material used in constructing the elongated panel and the thigh encircling portion is of a stretchable elastic, once the device is in position about the patient a force exerted on the edge portions 14c and 14d will cause the material to stretch and conform to the patent's body. When a feeling of comfortable support is achieved, the edges can quickly be interconnected together in the manner shown in FIG. 4 to positively secure the device in place. Once in position, the unique configuration of the device insures that it will remain in position on the amputee without causing discomfort and without shifting about.

To apply the necessary compressive forces to the stump to correctly shrink it, three elongated, angularly extending overlapping straps are permanently affixed at one end to the front surface 14a of the support panel (FIG. 1). The straps pass around the stump portion in the manner shown in FIG. 2 and are secured posteriorly using Velcro type self-gripping fastening means provided on the free ends of the straps and on the rear surface 14b of the support panel. As best seen in FIG. 1, these straps comprise first and second elongated straps 20 and 22 which depend from the front surface 14a of the support panel in a diagonally extending, crossing relationship. Each of the straps 20 and 22 have first and second ends 20a and 20b and 22a and 22b respectively. The first end portions 20a and 22a of the straps are secured as by sewing or other appropriate means to the front surface 14a of elongated panel 14. These end portions are secured to the support panel in a manner such that straps 20 and 22 extend diagonally, that is angularly with respect to one another defining an acute angle "A" proximate their crossing point (FIG. 1).

An elongated third strap 24 extends substantially vertically downwardly from support panel 14 in an overlapping crossing relationship with respect to first and second straps 20 and 22. Third strap 24 also has first and second ends 24a and 24b with end portion 24a being affixed as by sewing to the front surface 14a of elongated panel 14 (FIG. 3).

As illustrated in FIG. 2, a third fastening means, shown here as a nap surface "N", is provided on the rear surface 14b of the support panel 14. Provided on each of the ends 20b, 22b, and 24b of the straps, is a fourth fastening means shown here as Velcro hook surface pads "H".

Once the support panel 14 is in position on the amputee, and the side portions 14c and 14d and fastened together in the manner shown in FIGS. 1 and 4, the straps 20, 22, and 24 can be brought into uniform compressive engagement with the stump in the following manner. Beginning with strap 20, which starts from a medial location and extends to a lateral location, this strap is passed beneath the lower surface of the stump and anchored posteriorly of the device toward a medial location. Because the straps are preferably formed of a yieldable elastic material, the proper compressive force can be exerted on the stump and then the hook pad H securely fastened to the nap surface N carried on the rear surface of the panel 14 in the manner shown in FIG. 2. Next, strap 22 which extends laterally to medialy is passed beneath the other side of the stump and drawn tight to exert the appropriate upper compressive force on the stump. Strap 22 is then anchored posteriorly toward a lateral location by fastening the hook pad H to the nap surface N on the rear surface of the panel 14. With straps 20 and 22 anchored posteriorly, strap 24, which is the centrally located, downwardly extending strap, is passed beneath the central portion of the stump and stretched to exert the appropriate upward compressive force on the stump. To maintain strap 24 in this position and to assist in securing straps 20 and 24 in position the hook pad H provided on the lower end of strap 22 is also securely fastened to the nap surface carried by the rear surface of panel 14. With this construction, strap 24, in cooperation with straps 20 and 22, exerts a positive, uniform compressive force on the stump. The details of the locking inter-engagement of the hook surface pad with the nap surface on the elongated panel is illustrated in FIG. 5.

Because of the unique design of the apparatus of the invention as described in the preceding paragraphs, it can easily and correctly be applied either by the amputee himself or by relatively unskilled hospital workers. Similarly, when treatment of the stump is necessary the stump end can be quickly and easily exposed by merely disconnecting the hook surfaces H on the end portions of the straps from the nap surface on the rear surface of the support panel. The necessary treatment of the stump can then be accomplished and then the straps quickly and easily reattached to the nap surface of the support panel thereby reapplying uniform compressive forces to the stump portion.

While various materials can be used to construct the apparatus of the invention, elastic material of the character used in the manufacture of girdles has proven satisfactory for the construction of the elongated support panel 14 and the upper thigh encircling portion 14e. In the construction of the straps, 20, 22 and 24, various types of stretchable soft material can be used, but a material of the character used in the manufacture of bandages sold under the "Ace" trademark has proven quite satisfactory. Further, as previously mentioned, while Velcro type materials are preferable for use as the fastening means, it is apparent that other types of fastening arrangements could be used if desired for particular applications. For example, plastic zippers or like fasteners can be used to interconnect the edge portions 14c and 14d of the support panel and tape or similar fastening devices could be used to interconnect the end portions 20b, 22b and 24b of the straps with the posterior surface of the support panel 14.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A post surgical appliance for applying compressive forces to the stump of an above the knee amputee, comprising:
   (a) an elongated support panel of stretch material for encircling the lower abdominal portion of the amputee, said support panel having front and rear surfaces and overlapping edge portions;
   (b) first fastening means carried by one of said overlapping edge portions and second fastening means carried by the other of said overlapping edge portions, said first and second fastening means cooperating to releasably interconnect said edge portions;
   (c) third fastening means carried by said rear surface of said support panel;
   (d) first and second elongated straps depending from said support panel in a diagonally extending, crossing relationship, said first and second straps each having first and second ends, said first ends being connected to said front surface of said support panel;
   (e) a third elongated strap extending substantially vertically from said support panel in a crossing relationship with said first and second straps, said third elongated strap having first and second ends, said first end being connected to said front surface of said panel; and
   (f) fourth fastening means carried by said second ends of said first, second and third straps for releasable interconnection with said third fastening means carried by said rear surface of said support panel.

2. An appliance as defined in claim 1 including an upper thigh encircling portion of stretch material depending from one side of said elongated support panel.

3. An appliance as defined in claim 1 in which said first and second fastening means comprise self-gripping fastening means of the Velcro type, one of said first and second fastening means comprising a nap surface and the other of said first and second fastening means comprising a hook surface.

4. An appliance as defined in claim 1 in which said third and fourth fastening means comprise self gripping fastening means of the Velcro type, said third fastening means comprising a nap surface and said fourth fastening means comprising a hook surface.

5. A post surgical appliance for applying compressive forces to the stump of an above the knee amputee, comprising:
   (a) an elongated support panel of stretch material for encircling the lumbar region of the amputee, said support panel having front and rear surfaces and overlapping edge portions;
   (b) an upper thigh encircling portion of stretch material depending from one side if said elongated support panel;
   (c) first fastening means carried by one of said overlapping edge portions and second fastening means carried by the other of said overlapping edge portions, said first and second fastening means cooperating to releasably interconnect said edge portions;
   (d) third fastening means carried by said rear surface of said support panel;
   (e) first and second elongated straps depending from said support panel each having first and second ends, said first ends being connected to said front surface of said support panel;
   (f) a third elongated strap extending from said support panel in an overlapping relationship with said first and second straps, said third elongated strap having first and second ends, said first end being connected to said front surface of said panel; and
   (g) fourth fastening means carried by said second ends of said first, second and third straps for releasable interconnection with said third fastening means carried by said rear surface of said support panel.

6. A post surgical appliance for applying compressive forces to the stump of an above the knee amputee, comprising:
   (a) an elongated support panel of stretch material for encircling the lower abdominal portion of the amputee, said support panel having front and rear surfaces and overlapping edge portions;
   (b) a nap surface carried by one of said overlapping edge portions and a cooperating hook surface carried by the other of said overlapping edge portions, said napped and hook surfaces cooperating to releasably interconnect said edge portions;
   (c) third fastening means carried by said rear surface of said support panel;
   (d) first and second elongated straps depending from said support panel in a diagonally extending, crossing relationship, said first and second straps each having first and second ends, said first ends being connected to said front surface of said support panel;
   (e) a third elongated strap extending substantially vertically from said support panel in a crossing relationship with said first and second straps, said third elongated strap having first and second ends, said first end being connected to said front surface of said panel; and
   (f) a hook surface carried by said second ends of said first, second and third straps for releasable interconnection with said nap surface carried by said rear surface of said support panel.

7. An appliance as defined in claim 6 including a thigh encircling portion of stretch material integrally formed with and depending from one side of said elongated support panel.

* * * * *